(12) United States Patent
Barrett et al.

(10) Patent No.: US 11,810,532 B2
(45) Date of Patent: Nov. 7, 2023

(54) SYSTEMS FOR MONITORING AND REGULATING HARMFUL BLUE LIGHT EXPOSURE FROM DIGITAL DEVICES

(71) Applicant: Eyesafe Inc., Eden Prairie, MN (US)

(72) Inventors: Justin Barrett, Eden Prairie, MN (US); Paul Broyles, Cypress, TX (US); Derek Harris, Saint Paul, MN (US)

(73) Assignee: EYESAFE INC., Eden Prairie, MN (US)

( * ) Notice: Subject to any disclaimer, the term of this patent is extended or adjusted under 35 U.S.C. 154(b) by 0 days.

(21) Appl. No.: 17/734,968

(22) Filed: May 2, 2022

(65) Prior Publication Data

US 2022/0366870 A1  Nov. 17, 2022

Related U.S. Application Data

(63) Continuation-in-part of application No. 16/695,975, filed on Nov. 26, 2019, now Pat. No. 11,347,099.
(Continued)

(51) Int. Cl.
*G09G 5/10* (2006.01)
*A61N 5/06* (2006.01)

(52) U.S. Cl.
CPC ............ *G09G 5/10* (2013.01); *A61N 5/0618* (2013.01); *A61N 2005/0628* (2013.01);
(Continued)

(58) Field of Classification Search
CPC .......... H05B 47/10; H05B 47/11; G09G 5/10; G09G 2320/0626; G09G 2320/066;
(Continued)

(56) References Cited

U.S. PATENT DOCUMENTS

| 2,403,685 A | 7/1946 | Sachtleben et al. |
| 2,493,200 A | 1/1950 | Land |

(Continued)

FOREIGN PATENT DOCUMENTS

| CA | 2924278 A1 | 6/2008 |
| CN | 1545702 A | 11/2004 |

(Continued)

OTHER PUBLICATIONS

Final Rejection pertaining to corresponding U.S. Appl. No. 17/465,216, dated Sep. 30, 2022.
(Continued)

*Primary Examiner* — Jimmy T Vu
(74) *Attorney, Agent, or Firm* — GRUMBLES LAW PLLC; Brittany Haanan

(57) ABSTRACT

The present disclosure describes a wellness application for digital usage comprising at least one software program that identifies the level of high energy visible light reduction provided by the thin film; and a dosimeter for sending data about ionizing radiation to the software. The software tracks the total time of device usage and determines wherein the software, based on a dosimeter measurement received from the dosimeter, communicates with at least one processor to execute at least one of: determine a notification for reducing exposure to high energy visible blue light about divide user interface, and adjust the display output by at least one of adjusting a color contrast and brightness, taking into account the level of visible light coverage and total time of device usage.

19 Claims, 6 Drawing Sheets

Related U.S. Application Data

(60) Provisional application No. 63/322,523, filed on Mar. 22, 2022, provisional application No. 62/772,513, filed on Nov. 28, 2018.

(52) U.S. Cl.
CPC .......... A61N 2005/0663 (2013.01); A61N 2005/0667 (2013.01); G09G 2320/066 (2013.01); G09G 2320/0626 (2013.01); G09G 2320/0666 (2013.01); G09G 2354/00 (2013.01); G09G 2360/145 (2013.01); G09G 2380/08 (2013.01)

(58) Field of Classification Search
CPC ..... G09G 2320/0666; G09G 2360/145; G09G 2380/08; G09G 2354/00; G02B 5/22; G02B 5/208; G02B 6/0051; G02B 1/04; G02F 1/133514; G02F 1/133536; G02F 1/133603; G02F 1/133614; G02F 1/33607; G02F 2201/086; G02F 2201/0663; G05B 5/003; A61N 5/0618; A61N 2005/0628; A61N 2005/0663; A61N 2005/0667

See application file for complete search history.

(56) References Cited

U.S. PATENT DOCUMENTS

| | | |
|---|---|---|
| 3,382,183 A | 5/1968 | Donoian et al. |
| 3,482,915 A | 12/1969 | Ferrand |
| 3,687,863 A | 8/1972 | Paul |
| 4,618,216 A | 10/1986 | Suzawa |
| 4,842,781 A | 6/1989 | Nishizawa et al. |
| 4,878,748 A | 11/1989 | Johansen et al. |
| 4,966,441 A | 10/1990 | Conner |
| 4,989,953 A | 2/1991 | Kirschner |
| 5,083,252 A | 1/1992 | Mcguire |
| 5,177,509 A | 1/1993 | Johansen et al. |
| 5,446,569 A | 8/1995 | Iwai et al. |
| 5,483,464 A | 1/1996 | Song |
| 5,555,492 A | 9/1996 | Feger |
| 5,745,391 A | 4/1998 | Fopor |
| 5,952,096 A | 9/1999 | Yamashita et al. |
| 6,019,476 A | 2/2000 | Kirschner |
| 6,229,252 B1 | 5/2001 | Teng et al. |
| 6,295,106 B1 | 9/2001 | Fukuzawa et al. |
| 6,663,978 B1 | 12/2003 | Olson et al. |
| 6,778,238 B2 | 8/2004 | Moon et al. |
| 6,824,712 B1 | 11/2004 | Yang et al. |
| 6,826,001 B2 | 11/2004 | Funakura et al. |
| 6,846,579 B2 | 1/2005 | Anderson et al. |
| 6,955,430 B2 | 10/2005 | Pratt |
| 6,984,038 B2 | 1/2006 | Ishak |
| 6,991,849 B2 | 1/2006 | Oya |
| 7,014,336 B1 | 3/2006 | Ducharme et al. |
| 7,019,331 B2 | 3/2006 | Winters et al. |
| 7,019,799 B2 | 3/2006 | Utsumi et al. |
| 7,019,903 B2 | 3/2006 | Berger et al. |
| 7,029,118 B2 | 4/2006 | Ishak |
| 7,045,944 B2 | 5/2006 | Ushifusa et al. |
| 7,066,596 B2 | 6/2006 | Ishak |
| 7,071,602 B2 | 7/2006 | Terui et al. |
| 7,126,589 B2 | 10/2006 | Sung |
| 7,158,300 B2 | 1/2007 | Shimoda |
| 7,193,779 B2 | 3/2007 | Kim et al. |
| 7,218,044 B2 | 5/2007 | Kim et al. |
| 7,227,190 B2 | 6/2007 | Yasukawa et al. |
| 7,258,923 B2 | 8/2007 | Van Den et al. |
| 7,491,440 B2 | 2/2009 | Fukatani et al. |
| 7,520,608 B2 | 4/2009 | Ishak et al. |
| 7,524,060 B2 | 4/2009 | Ramos et al. |
| 7,556,376 B2 | 7/2009 | Ishak et al. |
| 7,572,028 B2 | 8/2009 | Mueller et al. |
| 7,579,769 B2 | 8/2009 | Wu et al. |
| 7,630,128 B2 | 12/2009 | Krieg-Kowald |
| 7,695,180 B2 | 4/2010 | Schardt et al. |
| 7,703,917 B2 | 4/2010 | Sanchez |
| 7,710,511 B2 | 5/2010 | Gehlsen et al. |
| 7,731,791 B2 | 6/2010 | Deno et al. |
| 7,755,276 B2 | 7/2010 | Wang et al. |
| 7,785,501 B2 | 8/2010 | Segawa et al. |
| 7,825,578 B2 | 11/2010 | Takashima et al. |
| 7,832,903 B2 | 11/2010 | Ramos |
| 7,884,545 B2 | 2/2011 | Yokoyama et al. |
| 7,914,177 B2 | 3/2011 | Sanchez et al. |
| 8,034,206 B2 | 10/2011 | Kim et al. |
| 8,044,942 B1 | 10/2011 | Leonhard et al. |
| 8,063,999 B2 | 11/2011 | Jabri et al. |
| 8,075,133 B2 | 12/2011 | Sanchez |
| 8,075,145 B2 | 12/2011 | Engblom et al. |
| 8,113,651 B2 | 2/2012 | Blum et al. |
| 8,164,844 B2 | 4/2012 | Toda et al. |
| 8,303,859 B2 | 11/2012 | Koo et al. |
| 8,323,357 B2 | 12/2012 | Feldhues et al. |
| 8,360,574 B2 | 1/2013 | Ishak et al. |
| 8,403,478 B2 | 3/2013 | Ishak |
| 8,487,331 B2 | 7/2013 | Jang et al. |
| 8,498,042 B2 | 7/2013 | Danner et al. |
| 8,500,274 B2 | 8/2013 | Ishak |
| 8,506,114 B2 | 8/2013 | Ven |
| 8,507,840 B2 | 8/2013 | Yu et al. |
| 8,518,498 B2 | 8/2013 | Song et al. |
| 8,547,504 B2 | 10/2013 | Guo et al. |
| 8,570,648 B2 | 10/2013 | Sanchez |
| 8,599,542 B1 | 12/2013 | Healey et al. |
| 8,657,455 B2 | 2/2014 | Yagi et al. |
| 8,659,724 B2 | 2/2014 | Hagiwara et al. |
| 8,680,406 B2 | 3/2014 | Chua |
| 8,680,492 B2 | 3/2014 | Ren et al. |
| 8,716,729 B2 | 5/2014 | Wiesmann et al. |
| 8,759,540 B2 | 6/2014 | Maeda et al. |
| 8,767,282 B2 | 7/2014 | Hashimura et al. |
| 8,770,749 B2 | 7/2014 | McCabe et al. |
| 8,817,207 B2 | 8/2014 | Rho et al. |
| 8,836,209 B2 | 9/2014 | Baek et al. |
| 8,882,267 B2 | 11/2014 | Ishak et al. |
| 8,928,220 B2 | 1/2015 | Ko et al. |
| 8,957,835 B2 | 2/2015 | Hoellwarth |
| 8,982,197 B2 | 3/2015 | Kim et al. |
| 9,051,232 B2 | 6/2015 | Kosuge et al. |
| 9,063,349 B2 | 6/2015 | Ishak et al. |
| 9,122,089 B2 | 9/2015 | Lee et al. |
| 9,287,471 B2 | 3/2016 | De et al. |
| 9,377,569 B2 | 6/2016 | Ishak et al. |
| 9,545,304 B2 | 1/2017 | Ishak et al. |
| 9,575,335 B1 | 2/2017 | Mccabe et al. |
| 9,798,163 B2 | 10/2017 | Ishak et al. |
| 9,814,658 B2 | 11/2017 | Ishak et al. |
| 9,927,635 B2 | 3/2018 | Ishak et al. |
| 10,247,980 B2 | 4/2019 | Cho et al. |
| 10,418,532 B2 | 9/2019 | Okubo |
| 10,649,129 B2 | 5/2020 | Chang et al. |
| 10,957,826 B2 | 3/2021 | Itoga et al. |
| 2002/0005509 A1 | 1/2002 | Teng et al. |
| 2002/0018890 A1 | 2/2002 | Sugimachi |
| 2002/0158574 A1 | 10/2002 | Wolk et al. |
| 2003/0214695 A1 | 11/2003 | Abramson et al. |
| 2004/0070726 A1 | 4/2004 | Ishak |
| 2004/0114242 A1 | 6/2004 | Sharp |
| 2004/0166342 A1 | 8/2004 | Wursche et al. |
| 2004/0181006 A1 | 9/2004 | Warren et al. |
| 2004/0232813 A1 | 11/2004 | Nakano et al. |
| 2004/0246413 A1 | 12/2004 | Stephenson et al. |
| 2005/0042531 A1 | 2/2005 | Lee et al. |
| 2005/0259082 A1 | 11/2005 | Potsch et al. |
| 2005/0275769 A1 | 12/2005 | Roh et al. |
| 2006/0012754 A1 | 1/2006 | Larson et al. |
| 2006/0040416 A1 | 2/2006 | Sano |
| 2006/0045989 A1 | 3/2006 | Minami |
| 2007/0013649 A1 | 1/2007 | Kim et al. |
| 2007/0030415 A1 | 2/2007 | Epstein |
| 2007/0058107 A1 | 3/2007 | Im et al. |

(56) References Cited

U.S. PATENT DOCUMENTS

| | | |
|---|---|---|
| 2007/0077410 A1 | 4/2007 | Shi |
| 2007/0078216 A1 | 4/2007 | Cao et al. |
| 2007/0146584 A1 | 6/2007 | Wang et al. |
| 2007/0195404 A1 | 8/2007 | Iijima |
| 2007/0216861 A1 | 9/2007 | Ishak et al. |
| 2007/0275184 A1 | 11/2007 | Lee et al. |
| 2008/0094566 A1 | 4/2008 | Ishak et al. |
| 2008/0137030 A1 | 6/2008 | Hoffman |
| 2008/0290787 A1 | 11/2008 | Cok |
| 2008/0297931 A1 | 12/2008 | Ramos |
| 2009/0058250 A1 | 3/2009 | Sin et al. |
| 2009/0105437 A1 | 4/2009 | Determan et al. |
| 2009/0128895 A1 | 5/2009 | Seo et al. |
| 2009/0173958 A1 | 7/2009 | Chakraborty et al. |
| 2009/0236622 A1 | 9/2009 | Nishihara |
| 2010/0022040 A1 | 1/2010 | Konishi et al. |
| 2010/0039704 A1 | 2/2010 | Hayashi et al. |
| 2010/0118511 A1 | 5/2010 | Wegat |
| 2010/0134879 A1 | 6/2010 | Yoshihara et al. |
| 2010/0231830 A1 | 9/2010 | Hirakata et al. |
| 2011/0019269 A1 | 1/2011 | Dirk |
| 2011/0043486 A1 | 2/2011 | Hagiwara et al. |
| 2011/0157546 A1 | 6/2011 | Ishak et al. |
| 2011/0176325 A1 | 7/2011 | Sherman et al. |
| 2011/0234079 A1 | 9/2011 | Eom et al. |
| 2011/0267801 A1 | 11/2011 | Tong et al. |
| 2011/0289654 A1 | 12/2011 | Williams et al. |
| 2011/0291132 A1 | 12/2011 | Liu et al. |
| 2011/0299168 A1 | 12/2011 | Combs |
| 2011/0299284 A1 | 12/2011 | Ven et al. |
| 2011/0315939 A1 | 12/2011 | Okayasu et al. |
| 2012/0021152 A1 | 1/2012 | Glaser et al. |
| 2012/0038861 A1 | 2/2012 | Lieshout et al. |
| 2012/0075577 A1 | 3/2012 | Ishak et al. |
| 2012/0113672 A1 | 5/2012 | Dubrow et al. |
| 2012/0120515 A1 | 5/2012 | Ishak et al. |
| 2012/0162106 A1 | 6/2012 | Choi et al. |
| 2012/0162752 A1 | 6/2012 | Kitano et al. |
| 2012/0217865 A1 | 8/2012 | Cabalu et al. |
| 2012/0300447 A1 | 11/2012 | Maxik et al. |
| 2012/0307194 A1 | 12/2012 | Croft et al. |
| 2013/0009059 A1 | 1/2013 | Caruso |
| 2013/0063493 A1 | 3/2013 | House |
| 2013/0156999 A1 | 6/2013 | Braesch et al. |
| 2013/0239874 A1 | 9/2013 | Smith et al. |
| 2013/0278134 A1 | 10/2013 | Ko et al. |
| 2013/0282115 A1 | 10/2013 | Ishak et al. |
| 2014/0009061 A1 | 1/2014 | Itoga et al. |
| 2014/0009912 A1 | 1/2014 | Wheatley et al. |
| 2014/0022779 A1 | 1/2014 | Su et al. |
| 2014/0049700 A1 | 2/2014 | Chen et al. |
| 2014/0078420 A1 | 3/2014 | Liu et al. |
| 2014/0093661 A1 | 4/2014 | Trajkovska et al. |
| 2014/0175505 A1 | 6/2014 | Yamazaki et al. |
| 2014/0233105 A1 | 8/2014 | Schmeder et al. |
| 2014/0350146 A1 | 11/2014 | Tsubouchi |
| 2014/0355106 A1 | 12/2014 | Laluet et al. |
| 2014/0363767 A1 | 12/2014 | Murakami et al. |
| 2015/0036379 A1 | 2/2015 | Lee |
| 2015/0098058 A1 | 4/2015 | De et al. |
| 2015/0124188 A1 | 5/2015 | Kadowaki et al. |
| 2015/0160478 A1 | 6/2015 | Ishak et al. |
| 2015/0187987 A1 | 7/2015 | Sim et al. |
| 2015/0212238 A1 | 7/2015 | Chang |
| 2015/0212352 A1 | 7/2015 | Guo et al. |
| 2015/0238308 A1 | 8/2015 | Ishak et al. |
| 2015/0248033 A1 | 9/2015 | Zhu et al. |
| 2015/0253653 A1 | 9/2015 | Fujita et al. |
| 2015/0277003 A1 | 10/2015 | Sanchez et al. |
| 2015/0311402 A1 | 10/2015 | Ven |
| 2015/0329684 A1 | 11/2015 | Kamimoto et al. |
| 2015/0338561 A1 | 11/2015 | Moe et al. |
| 2015/0378217 A1 | 12/2015 | Kim et al. |
| 2016/0126428 A1 | 5/2016 | Hosokawa et al. |
| 2017/0037308 A1 | 2/2017 | Römer et al. |
| 2017/0062529 A1 | 3/2017 | Paek et al. |
| 2017/0309235 A1 | 10/2017 | Garcia |
| 2017/0315405 A1 | 11/2017 | Masuda et al. |
| 2017/0363884 A1 | 12/2017 | Hallock et al. |
| 2018/0052362 A1 | 2/2018 | Kang et al. |
| 2018/0064616 A1 | 3/2018 | Ishak et al. |
| 2018/0107050 A1* | 4/2018 | Barrett .................. G02B 5/205 |
| 2018/0113327 A1 | 4/2018 | Ishak et al. |
| 2018/0284609 A1 | 10/2018 | Kandanarachch et al. |
| 2019/0004223 A1 | 1/2019 | Sanchez et al. |
| 2019/0103523 A1 | 4/2019 | Choi et al. |
| 2019/0121176 A1 | 4/2019 | Lee et al. |
| 2019/0196071 A1 | 6/2019 | Barrett et al. |
| 2019/0219751 A1 | 7/2019 | Barrett et al. |
| 2019/0285941 A1 | 9/2019 | Liu et al. |
| 2019/0312185 A1 | 10/2019 | Zhang et al. |
| 2020/0124781 A1 | 4/2020 | Tseng et al. |
| 2020/0166798 A1 | 5/2020 | Garbar et al. |
| 2020/0174168 A1 | 6/2020 | Barrett |
| 2020/0249520 A1 | 8/2020 | Barrett et al. |
| 2020/0286962 A1 | 9/2020 | Lee et al. |
| 2020/0303598 A1 | 9/2020 | Kim et al. |
| 2021/0043807 A1 | 2/2021 | Harris et al. |
| 2021/0098661 A1 | 4/2021 | Harris et al. |
| 2021/0116612 A1 | 4/2021 | Barrett et al. |
| 2021/0165276 A1 | 6/2021 | Garbar et al. |
| 2021/0273141 A1 | 9/2021 | Harris et al. |
| 2021/0311354 A1 | 10/2021 | Garbar et al. |
| 2022/0011627 A1 | 1/2022 | Barrett et al. |

FOREIGN PATENT DOCUMENTS

| | | |
|---|---|---|
| CN | 101216611 A | 7/2008 |
| CN | 101899222 A | 12/2010 |
| CN | 201666985 U | 12/2010 |
| CN | 102879920 A | 1/2013 |
| CN | 102898800 A | 1/2013 |
| CN | 202847016 U | 4/2013 |
| CN | 203410122 U | 1/2014 |
| CN | 103941320 A | 7/2014 |
| CN | 204213761 U | 3/2015 |
| CN | 104614786 A | 5/2015 |
| CN | 104950515 A | 9/2015 |
| CN | 105788474 B | 7/2016 |
| CN | 103448312 B | 10/2016 |
| CN | 106324908 B | 1/2017 |
| CN | 106950632 A | 7/2017 |
| CN | 107808919 A | 3/2018 |
| CN | 209782327 U | 12/2019 |
| DE | 202014000982 U1 | 3/2014 |
| EP | 0509727 A2 | 10/1992 |
| EP | 0855602 A2 | 7/1998 |
| EP | 0965034 B1 | 5/2007 |
| EP | 2085798 A1 | 8/2009 |
| EP | 2095177 A1 | 9/2009 |
| EP | 2096471 A1 | 9/2009 |
| EP | 2128889 A1 | 12/2009 |
| EP | 2260348 A2 | 12/2010 |
| EP | 1794240 B1 | 1/2013 |
| EP | 2874001 A1 | 5/2015 |
| EP | 3026485 A2 | 6/2016 |
| ES | 1094781 U | 12/2013 |
| FR | 2909779 A1 | 6/2008 |
| JP | 2001315240 A | 11/2001 |
| JP | 2003149605 A | 5/2003 |
| JP | 2003279988 A | 10/2003 |
| JP | 2006031030 A | 2/2006 |
| JP | 2006278980 A | 10/2006 |
| JP | 2007150228 A | 6/2007 |
| JP | 2007317896 A | 12/2007 |
| JP | 2010511205 A | 4/2010 |
| JP | 2010261986 A | 11/2010 |
| JP | 2011039093 A | 2/2011 |
| JP | 2013067811 A | 4/2013 |
| JP | 2013222212 A | 10/2013 |
| JP | 2013238634 A | 11/2013 |
| JP | 2014000819 A | 1/2014 |
| JP | 2014225030 A | 12/2014 |
| JP | 2016126064 A | 7/2016 |

(56) References Cited

FOREIGN PATENT DOCUMENTS

| | | |
|---|---|---|
| JP | 2016128931 A | 7/2016 |
| JP | 2017017317 A | 1/2017 |
| KR | 20030097143 A | 12/2003 |
| KR | 1020060048986 A | 5/2006 |
| KR | 20150075215 A | 7/2015 |
| KR | 20160066707 A | 6/2016 |
| KR | 101815619 B1 | 1/2018 |
| WO | 1988002871 A1 | 4/1988 |
| WO | 2002101695 A1 | 12/2002 |
| WO | 03010569 A2 | 2/2003 |
| WO | 2004090589 A1 | 10/2004 |
| WO | 2005034066 A1 | 4/2005 |
| WO | 2005106542 A1 | 11/2005 |
| WO | 2007075520 A2 | 7/2007 |
| WO | 2007109202 A2 | 9/2007 |
| WO | 2007146933 A2 | 12/2007 |
| WO | 2008024414 A2 | 2/2008 |
| WO | 2008067109 A1 | 6/2008 |
| WO | 2008068353 A1 | 6/2008 |
| WO | 2008106449 A1 | 9/2008 |
| WO | 2009123754 A2 | 10/2009 |
| WO | 2010111499 A1 | 9/2010 |
| WO | 2012006265 A1 | 1/2012 |
| WO | 2013123592 A1 | 8/2013 |
| WO | 2013176888 A1 | 11/2013 |
| WO | 2013188825 A1 | 12/2013 |
| WO | 2014055513 A1 | 4/2014 |
| WO | 2014077166 A1 | 5/2014 |
| WO | 2014096475 A1 | 6/2014 |
| WO | 2014155787 A1 | 10/2014 |
| WO | 2014196638 A1 | 12/2014 |
| WO | 2015179761 A1 | 11/2015 |
| WO | 2016179906 A1 | 11/2016 |
| WO | 2016205260 A1 | 12/2016 |
| WO | 2017039024 A1 | 3/2017 |
| WO | 2018137262 A1 | 8/2018 |
| WO | 2019099554 A1 | 5/2019 |
| WO | 2021108105 A1 | 6/2021 |
| WO | 2021108107 A1 | 6/2021 |

OTHER PUBLICATIONS

International Search Report and Written Opinion for International Application No. PCT/US2022/031930, dated Sep. 23, 2022.
Office Action pertaining to corresponding U.S. Appl. No. 17/091,152, dated Mar. 2, 2023.
International Search Report and Written Opinion for International Application No. PCT/US2022/050950, dated Mar. 9, 2023.
Office Action pertaining to Korean Patent Application No. 10-2021-7021455, dated Feb. 16, 2023.
International Search Report and Written Opinion for International Application No. PCT/US2015/032175, dated Aug. 28, 2015; date of filing: May 22, 2015; 10 pp.
International Search Report and Written Opinion for International Application No. PCT/US2016/037457, dated Sep. 16, 2016; date of filing: Jun. 14, 2016; 7 pp.
International Search Report and Written Opinion for International Application No. PCT/US2018/061103, dated Jan. 24, 2019; date of filing: Nov. 14, 2018; 6 pp.
International Search Report and Written Opinion for International Application No. PCT/US2020/059208, dated Feb. 5, 2020; date of filing: Nov. 5, 2020; 9 pp.
International Search Report and Written Opinion for International Application No. PCT/US2020/059308, dated Dec. 18, 2020; date of filing: Nov. 6, 2020; 8 pp.
International Search Report and Written Opinion for International Application No. PCT/US2021/052904, dated Dec. 27, 2021; date of filing: Sep. 30, 2021.
Kim, Boris F. and Bohandy, Joseph. "Spectroscopy of Porphyrins." Johns Hopkins APL Technical Digest, vol. 2, No. 1, 1981, pp. 153-163, www.jhuapl.edu/techdigest/views/pdfs/V02_N3.../V2_N3_1981_Kim. Retrieved Apr. 12, 2019.

Kodak advertisement. Buchsbaum, Ralph. Animals Without Backbones. The University of Chicago Press, 1948.
Li, Wei, "Solar Cell Materials and Applications Thereof", University of Electronic Science and Technology of China Press, Jan. 31, 2014, pp. 255-257.
Non-Final Office Action for U.S. Appl. No. 14/719,604; dated Aug. 24, 2016; date of filing: May 22, 2015; 41 pp.
Non-Final Office Action for U.S. Appl. No. 14/719,604; dated Aug. 30, 2017; date of filing: May 22, 2015; 59 pp.
Non-Final Office Action for U.S. Appl. No. 15/813,010; dated Nov. 6, 2020; date of filing Nov. 14, 2017; 9 pp.
Non-Final Office Action for U.S. Appl. No. 15/844,109; dated Sep. 4, 2019; date of filing Dec. 15, 2017; 49 pp.
Non-Final Office Action for U.S. Appl. No. 16/360,599; dated Jun. 28, 2019; date of filing: Mar. 21, 2019; 11 pp.
Non-Final Office Action for U.S. Appl. No. 16/695,983; dated Aug. 20, 2020; date of filing: Nov. 26, 2019; 15 pp.
Non-Final Office Action for U.S. Appl. No. 16/695,983; dated Jun. 30, 2020; date of filing: Nov. 26, 2019; 24 pp.
Non-Final Office Action for U.S. Appl. No. 16/696,516; dated Feb. 1, 2021; date of filing: Nov. 26, 2019; 9 pp.
Non-Final Office Action for U.S. Appl. No. 16/855,497; dated Jul. 1, 2020; date of filing: Apr. 22, 2020; 13 pp.
Non-Final Office Action for U.S. Appl. No. 17/121,695; dated Feb. 2, 2021; date of filing: Dec. 14, 2020; 11 pp.
Non-Final Office Action for U.S. Appl. No. 17/177,920; dated Apr. 15, 2021; date of filing: Feb. 17, 2021; 10 pp.
Office Action pertaining to corresponding Canadian Patent App. No. 3152206, dated Apr. 22, 2022.
Office Action pertaining to corresponding Canadian Patent App. No. 3154694, dated Apr. 27, 2022.
Office Action pertaining to corresponding Chinese Patent Application No. 201680048240.6, dated Sep. 13, 2021, 16 pages.
Office Action pertaining to corresponding Korean Patent Application No. 10-2021-7021453, dated Dec. 22, 2021.
Office Action pertaining to corresponding U.S. Appl. No. 17/348,570, dated Apr. 14, 2022.
Office Action pertaining to corresponding U.S. Appl. No. 17/465,216, dated Jun. 8, 2022.
Office Action pertaining to corresponding Chinese Patent Application No. 201680048240.6, dated Jul. 9, 2020.
Van Der Lely, et al., "Blue Blocker Glasses as a Countermeasure for Alerting Effects of Evening Light-Emitting Diode Screen Exposure in Male Teenagers," Journal of Adolescent Health, Aug. 2014, 7 pp.
Office Action pertaining to corresponding Chinese Patent Application No. 201680048240.6, dated Jan. 18, 2021.
Office Action pertaining to corresponding Korean Patent Application No. 20-2020-7000024, dated Aug. 19, 2021; 3 pp.
Perovich, B. W. "Black and White Filters Tutorial." Freestyle Photographic Supplies, www.freestylephoto.biz/black-and-white-filters-tutorial. Retrieved Apr. 12, 2019.
Richards, Bryce S. "Up- and Down-Conversion Materials for Photovoltaic Devices" Proceedings of SPIE—The International Society for Optical Engineering, 9 pp. Apr. 2012.
Search Report and Examination Opinion for European Application No. 15796219.2; dated Dec. 8, 2017; date of filing: May 22, 2015; 7 pp.
Search Report and Examination Opinion for European Application No. 15796219.2; dated Mar. 26, 2019 Tate of filing: May 22, 2015; 5 pp.
Second Office Action for C.N. Application No. 201580040377.2 (national phase of PCT/US2015/032175); dated Jan. 2, 2019; date of filing: May 22, 2015; 12 pp.
Second Office Action for Chinese Application No. 201880073490.4 (English Translation); dated Apr. 20, 2021; date of filing: May 13, 2020; 8 pp.
Second Office Action for J.P. Application No. 2017-032775 (national phase of PCT/US2015/032175); dated Feb. 4, 2020; date of filing: May 22, 2015; 22 pp.
Second Office Action for Japanese Application No. 2020-526348 (English Translation); dated Aug. 3, 2021; date of filing: May 13, 2020; 6 pp.

(56) References Cited

OTHER PUBLICATIONS

Simmons, Adam "The Evolution of LED Backlights." PC Monitors www.pcmonitorsinfo/articles. Retrieved May 1, 2017.
Sun, Shunqing, "Research on Organic Optical Information Storage Materials—Optical, Thermal and Thin Film Optical Properties of Indoles Cyanine Dyes", Post-doctoral Research Report of Institute of Photographic Chemistry of the Chinese Academy of Sciences, Dec. 31, 1993, pp. 6-7.
Sunstone Luminescent UCP Nanocrystals, sigmaaldrich.com, 7 pp. Retrieved Apr. 17, 2017.
Supplementary European Search Report and Written Opinion for EP Application No. 18879246.9, dated Dec. 18, 2020; date of filing: Nov. 14, 2018; 5 pp.
Office Action pertaining to corresponding Japanese Patent App No. 2021-541465, dated Jun. 28, 2022.
Office Action pertaining to corresponding Japanese Patent App No. 2021-542506, dated Jun. 21, 2022.
Office Action pertaining to corresponding U.S. Appl. No. 17/348,570, dated Aug. 8, 2022.
"1002 nm NIR Dye", Technical Data Sheet, Product Code: NIR1002A, QCR Solutions Corp, Version 2011.NIR Dyes, www.qcrsolutions com, 1 page.
"ADS640PP Product Specification", American Dye Source, Inc., Retrieved at <>, Retrieved on May 18, 2015, 1 page.
"Filters for Color Photomicrography," Olympus America Inc., Olympus Microscopy Resource Center, http://www.plympusmicro.com/primer/photomicrography/colorfilters.html, Mar. 2012, 7 pp.
"Kentek Laser Safe Window Protection", Retrieved at <>, 1 pp. Retrieved on Apr. 28, 2014.
"Laser and fluorescent dyes, UV and NIR dyes, security inks and other optically functional materials", Retrieved at http://www.fabricolorholding.com/product, 2 pp. Retrieved May 18, 2015.
"LUM690 Near Infrared Dye", Moleculum, moleculum.com, Jan. 2015, 2 pages.
"LUM995 Near Infrared Dye", Moleculum, moleculum.com, Jan. 2015, 2 pages.
"Near Infared Dye: LUM1000A", Moleculum, moleculum.com, Jan. 2015, 1 page.
"Reticare, the first ocular protector for electronic device screens to launch at CES 2014"; https://www.reticare.com/tienda/en/blog/post/3-reticare-the-first-ocular-protector-for-electronic-device-screens-to-launch-at-ces-2014; Jan. 10, 2014; 7 pp. Retrieved Nov. 30, 2017.
"Tinuvin P Benzotriazole UV Absorber", Ciba Specialty Chemicals, Inc.,Printing Date: Aug. 1998, 2 pages.
"XGear Krystal Sapphire Screen Protector Film Shield For Apple IPhone 4 4S", Retrieved at <>, 3 pp. Retrieved Apr. 28, 2014.
"1031 nm NIR Dye", Technical Data Sheet, Product Code: NIR1031M, QCR Solutions Corp, Version: 2011.NIR Dyes, www.qcrsolutions. com, 1 page.
"1072 nm NIR Dye", Technical Data Sheet, Product Code: NIR1072A, QCR Solutions Corp, Version: 2011.NIR Dyes, www.qcrsolutions. com, 1 page.
"1073nm NIR Dye", Technical Data Sheet, Product Code: IR Dye 1151, Adam Gates & Company, LLC, www.adamgatescompany. com, 1 page.
"290 nm UV Dye", Technical Data Sheet, Product Code: UV290A, QCR Solutions Corp, Version: 2011.UV Dyes, www.qcrsolutions. com, 1 page.
"530 nm Visible Dye", Technical Data Sheet, Product Code: VIS530A, QCR Solutions Corp, Version: 2011.VIS Dyes, www.qcrsolutions. com, 1 page.
"675 nm Visible Dye", Technical Data Sheet, Product Code: VIS675F, QCR Solutions Corp, Version: 2011 VIS Dyes, www.qcrsolutions. com, 1 page.
"ABS 668: Visible Narrow Band Absorber", Exciton, Inc., www.exciton.com, 1 page.
"ABS 691: Visible Narrow Band Absorber", Exciton, Inc., www.exciton.com, 1 page.
"Capturing All the Light: Panchromatic Visible Absorption for Solar Photoconversion." U.S. Department of Energy, Basic Energy Sciences, Jun. 1, 2014, science.energy.gov/bes/highlights/2014/bes-2014-06-g/. Retrieved Apr. 12, 2019.
"Dye Vis 347", Adam Gates & Company, LLC, www.adamgatescompany.com, 1 page.
"Dye Vis 670", Adam Gates & Company, LLC, www.adamgatescompany.com, 1 page.
"DYE VIS 671", Adam Gates & Company, LLC, www.adamgatescompany.com, 1 page.
"Infrared Dye 1422", Adam Gates & Company, LLC, www.adamgatescompany.com, 1 page.
"New ANSI/ISEA Z87. Jan. 2010 Standard", Uvex by Sperian, 2 pages.
"Spectral-Transmittance Bar Charts for Selected Kodak Wratten Filters." google search (www.google.com), search terms: kodak wratten filters bar chart, second image (wratten filter specs, iclane. net). Retrieved May 16, 2019.
A-594-5 Invisible Blue Pigment, dayglo.com, 1 page. Retrieved Jun. 2, 2019.
Abramowitz, Mortimer and Davidson, Michael W. "Kodak Color Compensating Filters Yellow." Olympus Microscopy Resource Center. olympus-lifescience.com. Retrieved May 16, 2019.
Andres Cantarero; Raman scattering applies to materials science; ScienceDirect; 2015; pp. 113-122; vol. 9; Elsevier.
ANSI Z80.3-2015, Nonprescription Sunglass and Fashion Eyewear Requirements, 41 pp.
ASTM International E 313-05; Standard Practice for Calculating Yellowness and Whiteness Indices from Instrumentally Measured Color Coordinates; Article; 6 pp.
Doeffinger, Derek, editor. Using Filters. Eastman Kodak Company, 1988. The Kodak Workshop Series, pp. 11, 13, 17, 46, 68-69.
dbay.com, screenshot of ebay purchase of Apr. 23, 2019. Retrieved May 16, 2019.
Examination Report pertaining to corresponding Australian Patent App. No. 2020392315, dated Mar. 31, 2022.
Examination Report pertaining to corresponding Australian Patent App. No. 2020393812, dated Mar. 30, 2022.
Extended European Search Report pertaining to European Patent Application No. 20891730.2, dated Dec. 14, 2021.
Final Office Action for U.S. Appl. No. 14/719,604; dated Mar. 28, 2017; filed May 22, 2015; 66 pp.
Final Office Action for U.S. Appl. No. 15/844,109; dated Jan. 16, 2020; filed Dec. 15, 2017; 12 pp.
Final Office Action for U.S. Appl. No. 16/855,497; dated Sep. 22, 2020; filed Apr. 22, 2020; 12 pp.
First Office Action for C.N. Application No. 201580040377.2 (national phase of PCT/US2015/032175); dated Feb. 24, 2018; date of filing: May 22, 2015; 5 pp.
First Office Action for C.N. Application No. 201680048240.6 (national phase of PCT/US2016/037457); dated Jan. 16, 2020; date of filing: Jun. 14, 2016; 10 pp.
First Office Action for Chinese Application No. 201880073490.4 (English Translation); dated Feb. 1, 2021; date of filing: May 13, 2020; 9 pp.
First Office Action for J.P. Application No. 2017-032775 (national phase of PCT/US2015/032175); dated May 15, 2019; date of filing: May 22, 2015; 6 pp.
First Office Action for Japanese Application No. 2020-526348 (English Translation); dated Mar. 11, 2021; date of filing: May 13, 2020; 6 pp.
Fonseca, "Apple patents a virtual reality headset for iPhone," http://vr-zone.com/articles/apple-patents-virtual-reality-headset-iphone/87267.html, Jun. 22, 2015, 4 pp.
Fritz, Norman L. "Filters: An Aid in Color-Infrared Photography." Photogrammetric Engineering and Remote Sensing, vol. 43, No. 1, Jan. 1977, pp. 61-72, www.asprs.org/wp-content/uploads/pers/1977journal/../1977_jan_61-72. Retrieved Apr. 4, 2019.
Gallas, Jim and Eisner, Mel; Chapter 23—Eye protection from sunlight damage; Journal; 2001; 437, 439-455; vol. 3. Comprehensive Series in Photosciences, Elvesier, abstract only.
Giovannetti, Rita. "The Use of Spectrophotometry UV-Vis for the Study of Porphyrins." Macro to Nano Spectroscopy, Uddin, Jamal (Ed.), IntechOpen Limited, 2012, pp. 87-108, www.intechopen.com/

(56) References Cited

OTHER PUBLICATIONS books/macro-to-nano-spectroscopy/the-use-of-spectrophotometry-uv-vis-for-thestudy-of-porphyrins. Retrieved Apr. 12, 2019.
Illuminant D65, 4 pp.
International Patent Application No. PCT/US2021/052904, filed Sep. 30, 2021.
Extended European Search Report pertaining to European Patent Application No. 20893018.0, dated Dec. 20, 2022.
Office Action pertaining to Japanese Patent Application No. 2021-542506, dated Dec. 20, 2022.
Office Action pertaining to corresponding U.S. Appl. No. 17/876,399, dated Mar. 30, 2023.
Japanese Office Action pertaining to corresponding Japanese Patent Application No. 2022-520547, dated May 23, 2023.
Examination Report pertaining to corresponding European Patent Application No. 20891730.2, dated May 2, 2023.

\* cited by examiner

SYSTEMS FOR MONITORING AND REGULATING HARMFUL BLUE LIGHT EXPOSURE FROM DIGITAL DEVICES

CROSS-REFERENCE TO RELATED APPLICATIONS

This application is a continuation-in-part of U.S. patent application Ser. No. 16/695,975, filed Nov. 26, 2019, which claims priority to U.S. Provisional Patent Application No. 62/772,513, filed Nov. 28, 2018. This application also claims the benefit of U.S. Provisional Application No. 63/322,523, filed Mar. 22, 2022. All references cited within are incorporated herein by reference in their entirety.

FIELD

The present invention relates to a software system for reducing light emission of portions of the light spectrum that can be done with or without the presence of a blue light filter.

BACKGROUND

Electronic devices, such as portable electronic display devices typically emit a visible light spectrum of which humans are able to detect wavelengths from about 380 nm to about 740 nm. Recently, it has been appreciated that certain characteristics of this light may be harmful to the user, and may lead to health symptoms and reactions, such as but not limited to eye strain, dry and irritated eyes, and headaches. Studies suggest that cumulative and prolonged exposure to the high-energy wavelengths of the visible blue light spectrum (380 nm -500 nm) emitted from digital screens may be leading to various health issues such as, but not limited to, those listed above. Within the high-energy visible light spectrum (380 nm -500 nm), a narrower band has been recognized as especially harmful (415 nm-455 nm).

Some solutions have been proposed and implemented to reduce these especially harmful wavelengths emitted from electronic devices. For example, physical filters, software programs, or applications are available which may be able to manage harmful light emissions within the visible light spectrum including the 380 nm-740 nm.

However, implementations of filters and/or software suffer drawbacks that hinder the user experience or efficacy of light management within the high-energy visible blue light spectrum. Software solutions alone typically impact the entire visible light spectrum, which leads to significant impact to the color temperature and overall system color accuracy. Physical filters alone typically have limitations to coverage across the blue light spectrum and may also impact the system color.

Another drawback to using software filtration of the high-energy visible light spectrum emitted from electronic devices is that there are limitations to the management of narrow bands of light recognized as especially harmful (415 nm-455 nm). Existing solutions for managing high-energy blue light including those shown in FIG. 2 have an inability to reduce only the harmful band of light, therefore impacting the system color. Additionally, the electronic device user has the ability to turn on or off the software, allowing for unfiltered light from the harmful light band without manual adjustment.

Additionally, it is recognized that exposure to high-energy visible blue light is cumulative in terms of causing adverse health effects. Existing solutions do not take into account the cumulative intake of high-energy visible blue light and are unable to intelligently adjust the system based on this information.

SUMMARY

Therefore, a need exists in the field for a software application that is able to recognize cumulative exposure and adjust levels of high-energy blue light in accordance with time exposure and other factors. Additionally, there are certain pre-existing conditions and other factors including, for example, age, where intelligent systems can be used to manage high-energy visible blue light. Intelligent systems combining a physical filter and software allows for automatic or logical adjustment to blue light emission from the display device, which may be automatic or in accordance with logic. Software with machine learning and artificial intelligence ("AI") can further use data to help the user interface with computing devices and lighted displays in a safer way and may improve the user's experience. In some embodiments, a novel physical filter may be integrated with a device display and combined with the software.

The present disclosure includes a software system to adjust the high-energy blue light spectrum in accordance with factors including time exposure of the electronic devices. The system may also include a novel physical filter integrated with the construction of the electronic device display (for example, in the display stack). The physical filter may be positioned on the device screen or within the construction of the screen with the software application providing adjustment of the spectrum relative to the properties of the physical filter. In some embodiments, the electronic device hardware utilizes the camera and software to adjust the light emissions based on factors including total device time usage, ambient lighting, and distance from the display. In other embodiments the computing device may use various user input and hardware to collect data about the user to further improve the user's interface.

The application may be used to improve eye health of the user and improve eye strain and comfort while using digital devices. The application may also improve circadian rhythms in an ever-increasing digital world. The application may also be used in conjunction with other digital products and software to improve the user experience using digital devices. The application determines dosage of harmful (radiation) blue light toxicity and modifies exposure in real-time as well as looks at the user's use, device settings and time blocks to help the user reduce blue light exposure.

The application may improve eye health by reducing digital eye strain. The application may also improve or reduce the risk of macular degeneration. The reduction of blue light toxicity may also improve circadian rhythms. Blue light is hazardous and reduction of exposure improves the user's eye health and wellness, in addition to improving the user's digital use experience.

Features and advantages of the present disclosure will be more readily understood from the following detailed description which should be read in conjunction with the accompanying drawings.

BRIEF DESCRIPTION OF THE DRAWING

The drawings are schematic illustrations and are not intended to limit the scope of the invention in any way. The drawings are not necessarily to scale. Some embodiments of the present invention are illustrated as an example and are not limited by the figures of the accompanying drawings, in which like references may indicate similar elements and in which.

DETAILED DESCRIPTION

The terminology used herein is for the purpose of describing particular embodiments only and is not intended to be limiting of the invention. As used herein, the term "and/or" includes any and all combination of one or more of the associated listed items. As used herein, the singular forms "a", "an", and "the" are intended to include the plural forms as well as the singular forms, unless the context clearly indicates otherwise. It will be further understood the terms "comprises" and/or "comprising", when used in this specification, specify the presence of stated features, steps, operations, elements and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity this description will refrain from repeating every possible combination of the individual steps in an unnecessary fashion. Nevertheless, the specification and claims should be read with the understanding that such combinations are entirely within the scope of the invention and the claims.

New software application systems for managing high-energy blue light as an intelligent system as well as new physical device filters for optionally managing light in combination with the software application systems as an intelligent system are discussed herein. In the following description, for purposes of explanation, numerous specific details are set forth in order to provide a thorough understanding of the present disclosure. It will be evident, however, to one skilled in the art that the present invention may be practiced without these specific details.

The present disclosure is to be recognized as an exemplification of the disclosure and is not intended to limit the disclosure to the specific embodiments illustrated by the figures or description below. The present disclosure will now be described by referencing the appended figures representing preferred embodiments.

Figure 1:
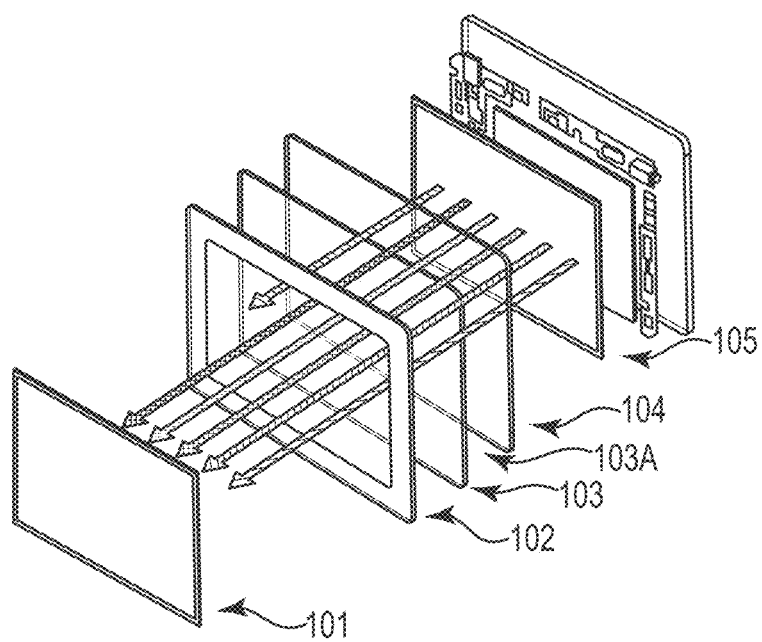
FIG. 1 is an exploded perspective view of a portion an embodiment of the disclosed filter.
Figure 2:
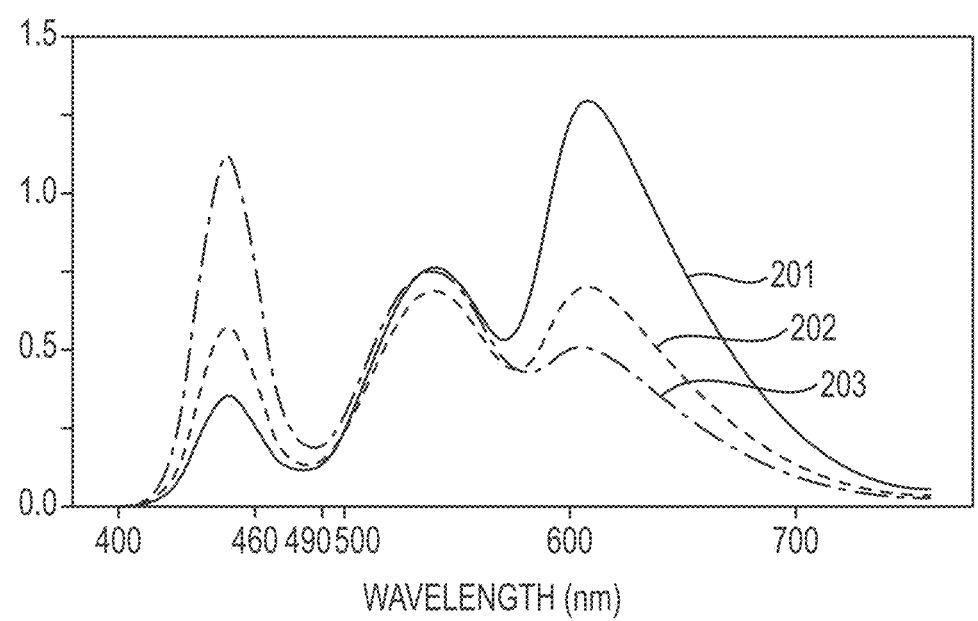
FIG. 2 is an illustration of the emission spectra for typical software only systems for the management of the high-energy visible blue light according to prior art.

FIG. 1 depicts an exploded perspective view of the elements that may comprise an electronic device display, representative of the construction of an LCD (liquid crystal display) display (the "device") according to various embodiments of the present invention.

In some embodiments, an OLED (organic light-emitting diode device) display may be used instead of an LCD display. While a computer or monitor display is illustrated herein, other displays, such as mobile device displays, television screens, and AR/VR displays may incorporate the software systems and/or physical filters described herein.

In preferred embodiments, a physical filter that provides the purpose of light filtration specific to the high-energy visible blue light spectrum (380 nm-500 nm), or specific to the harmful blue light spectrum (415 nm-455 nm), is included within the construction. FIG. 1 depicts the physical filter applied to the cover glass 103A, however the filter may be applied to other layers shown.

The physical filter providing light management according to these light spectrums may come in forms including a thin film, optically clear adhesive, or other physical barrier providing light management of the high-energy visible light spectrum (the "physical filter"). In some embodiments, the physical filter may be applied within the display construction including application to the interior of the cover glass or the polarizer.

Figure 3:
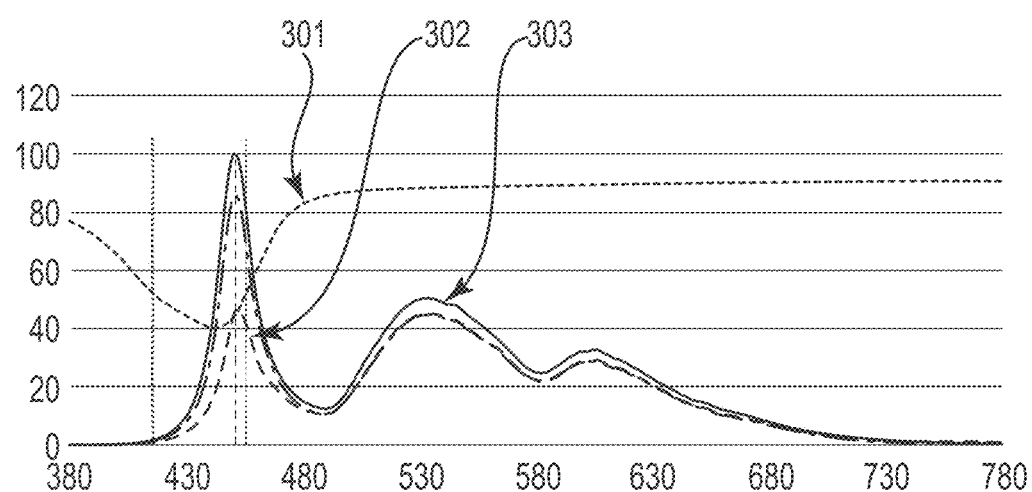
FIG. 3 is an illustration of the emission spectra for an embodiment of a disclosed physical filter.

As shown in FIG. 3, the physical filter applied to the device provides light management properties specific to the UV and high-energy visible blue light spectrum.

This integrated barrier within the device provides protection from UV light (<380 nm), high-energy visible blue light (380 nm-500 nm) and may selectively filter the narrow harmful band of blue light (415 nm-455 nm). Line 301 indicates light transmission, and lines 302 and 303 illustrate the absorbance of different physical filters that can be used in the system.

The software application can provide recognition of the filtration provided by the physical filter in FIG. 3. The software application can identify the level of coverage to the high-energy visible blue light spectrum provided by the physical filter to the user. Additional coverage levels are identified by the software application in addition to that provided by the physical filter. The software can provide tracking of the total time of device usage ("screen time") and adjust the level of blue light coverage in relation and automatically.

Alternatively, in some embodiments, the software application may operate without the presence of the physical filter or may not recognize alterations in light transmittance provided by the filter (for example, the software may only be able to read the hazard of the display's settings).

As the user's screen time increases, the software system can adjust the level of blue light coverage. The automatic adjustment of blue light coverage may also take into account factors including the age of the user or preexisting medical conditions including Age Related Macular Degeneration (AMD), dry eye or other eye, sleep, and health conditions. Additionally, the user has the ability to manually adjust the coverage levels.

The electronic device hardware may utilize the front facing camera to detect the distance of the device from the user, ambient lighting in the space, and other potential factors, and as a result adjust the coverage levels.

Figure 4:
FIG. 4 illustrates some of the many goals of encouraging digital wellness and total health.

FIG. 4 illustrates digital considerations for vision wellness and total health. In the illustration, hardware may be improved and integrated in devices that provide base level of protection from high-energy light. In one embodiment, software screen time and blue light exposure software dynamically and personally adjust light levels and encourage healthy choices. In other embodiments, healthcare AI may be used to guide product design and actions personalized for the user. The platform may integrate systems and platforms that include biometrics, navigation, behavior, and wellness.

Hardware and software integration may in some embodiments improve the user experience by improving the health and wellness of the user while interacting with the application. In one embodiment, utilizing hardware and software for the program for improved user experience may include, but is not limited to, programming, processing, agnostic, sensing, hardware fusion and integration with the applications. In some embodiments, the software receives data from the hardware components and uses AI processing for delivering the next-generation learning and developing the next generation of use. The software may perform operations both at, before, and after the OS platform.

In further embodiments, hardware and enabling software together may improve the user interface as data received enables more operations to occur. One type of hardware that may be implemented is a dosimeter, which is used to measure ionizing radiation over a given period of time. In some embodiments, the dosimeter measure brightness, and can measure blue light hazard ("BLH") of up to 100%. The application may track time, so that the dosimeter measurement is associated with a time period and frequency, so radiation exposure may be better determined. The dosimeter may also include presence detection of the user, or of objects, or another sensor may be utilized, and the presence data is sent and used for further wellness and health determinations.

In other embodiments, the dosimeter data may also be used for or in conjunction with facial recognition techniques, for identifying a person, facial expressions, movement, position relative to the device, biometrics, gestures, hand to face relativity, rubbing eyes, blinking, emotions, straining eyes, and other factors when using a digital device. Dosimeter data and communication may occur across multiple devices that keeps cumulative hazard information and data in the cloud. For the software modules to execute software on computing devices including all different types of apps, such as Android/iOS apps, the software modules then may send information to the cloud, or remote server, with the received data, in one non-limiting embodiment, distance from display, factored in with an association to the user or user's identification, and may be stored.

A personal computer ("PC") or other type of monitor/display may include an AI processor (or types semiconductor), such as a field programmable gate arrays ("FPGA") in some embodiments. Processors may be configured or have the capability to analyze video streams in real-time, and in some embodiments, with AI capabilities. The PC or monitor/display may be configured with the processor attached to other hardware such as a video source, such as a webcam and/or other sensors, via an electrical signaling interface. The processor receives the video and/or sensor data of the user while using the device. The software may in some instances be user configurable for hardware, software, system, device settings, and other environment configuration, and may be tracked at various levels (personal, aggregate with presence, aggregate ON time). Software may be running on any type of processor that is able to insert itself in the video stream and monitor it and make changes. This processor could be a scalar in a TV or monitor, an AP in a TV or monitor, and PC or other device AP (including in device driver), or a dedicated FPGA/AI processor between source and line driver signal output the display panel.

In one embodiment the detected user movement, gesture, position and other data of the user is received by the hardware on the computing device. In other examples, a server in a network may be accessed to get user identification. The network may be with another company, service, or community, and in other embodiments, the network may be part of the same user group. The identification request sent to the network may be for receiving a user's identification or identifier. The identification or identifier may include information about the user, a user associated number, and/or data about the user during use of the device. User information may include face expressions, facial gestures, motion, obstructions to device, distance from screen, blinking, squinting, position, glasses worn, facial recognition, gaze, presence (of anyone, organized people, of ON time), eyes closed, body movement, distance of head to the display/camera, distance of hands and other body parts to face, distance of hands to eyes, eye rubbing, obstructions between eyes and device, facial expressions, user characteristics, eye coverings, sound, light information of the environment and/or the device, etc. about the user or the user's environment. In some embodiments, user information may also include biometric data that may be acquired, such as temperature, heart rate, ergonomics, etc. The device may acquire other data related to the user that is used or stored as user information. The user information is received and used in conjunction with the user's use of the device, and in some instances with the device settings, to determine the cumulative risk of blue light toxicity.

Some functions may use data in different categories to determine user health. In one embodiment, squinting or other facial feature movement, gestures, eye to hand, head position, etc. may be analyzed by the software module or AI module, and the system may use this information for determining blink rates. The system may look at aggregate information over time and within a period of time, to determine changes, abnormality, user preferences and other deviations from a likely "normal" or most common user interaction. One example of when these same types of methods and cloud data aggregation may occur is with blink rates. This aggregated information may then be utilized for detecting and determining that the user may be doing an action that is not healthy, such as squinting, and may suggest that the user may need glasses. The system may use other, possibly older, data that identified the user as wearing glasses during use. A reminder may appear as a notification to wear glasses, to see a doctor, that the settings are poor, etc., or the system may adjust the settings responsively, such as enlarge the font or increase the brightness.

The computing device, hardware, or software may have settings that modules or the user may adjust, for example setting a time basis, making monitoring cumulative, a time of day, holiday, day of the week, etc. The adjustable settings may also be a running odometer of times and time periods (e.g., daily, weekly monthly, annually, etc.) for monitoring and data collection. Based on this time setting, limits may be set (e.g. daily limits, weekly limits, monthly limits, running odometer, etc.), so the toxic exposure may be limited. Other controls to reduce toxic exposure may also be allowed such as, but not limited to, color change and/or limit color. Dynamically controlling color may also be done by controlling the change per dosage (exposure amount during a period of time). Limits of brightness may also be set, as well as the change in brightness that is allowed. Dynamic changes to brightness may be accomplished by controlling brightness and changing it per dosage or exposure. Thresholds and limits may be identified, and once reached or exceeded, then the change in the setting may occur.

In some embodiments, the red, green, and blue colors emitted from an output display may have a value. The values, which represent the levels of emission, may be determined for each light color. These light color values are then considered with the interaction of the user.

In some embodiments, the system can track gaze detection. In other words, the system can track the amount of time a user spends focusing on nearby objects such as the display screen, and the system may then apply a 20/20/20 rule. In an embodiment, the rule may request the user looks at something that is "20 feet away, for 20 seconds, every 20 minutes." A possible responsive suggestion or notification to when the user is not following the 20/20/20 rule is the system determining and sending the instruction to the output display: "After 15 minutes of rest, and after 2 hours of continuous screen use, rest your eyes for 15 minutes." Other warnings may also be determined when approaching limits. Other warnings or notification may also be sent, such as when gaze is monitored, then the notification may indicate that the user should "look away" or "take a break" or some other instruction. When there is an unfocused 3D image, then the system may determine that changes to eye focus and time likely would improve health. The system may also determine that settings should be adjusted.

At least one module may run on the device. The modules are protocols or software that the device can execute to carry out the process. Each module can run on at least one application processor of one device, or in other embodiments more than one connected device.

In some embodiments, the received data may be stored for further use or post access and comparison after the real-time use. The user information data may be used to identify the user, to indicate the user's interaction with the device during use and may be used for other user and/or device related indicators. In some embodiments the data and user information may be stored locally or passed to a cloud service or network. The data and user information may be aggregated and associated with a user. In another embodiment, the data and user information may be stored across multiple devices (smart phones, mobile computing devices, smart watches, tablets, desktop computers, laptops, notebooks, personal computers, etc.).

Other module(s) may be implemented to interact with the hardware. In one embodiment, executing module(s) may determine or indicate and control device settings. In one embodiment, a module may control or provide information about the brightness of the device or display of the device. Other modules may be used in association with video components. Modules may be executed in parallel or as part of the video stream. In one embodiment, the modules may analyze, control, or modify content of the video stream that may be part of the graphical user interface display. Modules may impact or control brightness, such as reducing brightness.

In some embodiments, the function may be carried out by other components, such as in the instance of brightness change. Automatic brightness reduction may be based on all dosimeter functions and may or may not have color change in addition to brightness change. The hardware, such as the dosimeter, may require an interface for communication with other hardware, such as the monitor, graphics driver, or collection of data via EDID, and other possible hardware and hardware interfaces. The data collection may communicate from each monitor with other interfaces, such as I2C and EDID and USB alt channel communications, and in real-time and determinations are sent per event, session, time, per device monitor detection when the system determines that notifications or adjustments should be sent.

The graphics driver may be implemented for functionality and/or communication with the display. The system may include multiple modules with user interfaces, or a single one. There could be a refresh rate for updating data or monitor the processing and data exchange. The process of software executing could be part of a drive or working with a driver. The software modules could be either part of or in communication with the driver.

In some embodiments, the system may detect the type of display and lookup information on the blue light energy dosage of the display and may work with multiple displays as well. In the case where the display implements a data interface over I2C or USB (or other) between the AP and display, an API to request information for the display is claimed. This information includes the blue light hazard of the display with full brightness, and the current brightness setting. The API also allows the brightness to be changed. This interface also allows the blue primary to be reduced by scaling less than 100% as specified.

In one non-limiting instance, the monitor is plugged into a computing device. The module puts out x brightness; this one is set to y brightness; then sends a message to lower to 52% and drop blue level and red amount, improving the communication and remote control.

In a similar interface example, there may be an automatic reduction of blue light in red, green and blue light, and data may be based on all dosimeter functions. Similarly, this may be true for other types of color changes. The dosimeter may then continue to receive data about the colors after the color change and monitor associated with time, time period, or a set time. As in the earlier embodiment, the hardware and software may use an interface to monitor or graphics driver (or collection of data from via EDID, etc.).

Modules may read or control color contrasts of displays. In one embodiment, the red, green, and blue numbers (and possibly other light wavelengths associated with color wavelength ranges) may be determined. The colors may be impacted by lowering the values, and thus reducing the intensity or brightness of one or more selected colors, altering the display output. All three colors may, in some embodiments, be lowered, reducing the overall brightness. In other words, color impact may occur when there is a change in a specific number. One type may be when the blue balance is adjusted to affect impact and then control brightness overall. Adjustment may be based on user preference. In another embodiment, color adjustments may be made based on user input, device adjustments, or based on values compared to thresholds. Applying thresholds is one technique implemented to make adjustments. In another embodiment, algorithms may be applied to determine color adjustments of the output display. Other techniques are possible. In one embodiment, setting limits or adjustments to color on a daily, weekly, monthly or other regulated basis. There may also be notifications that appear to the user warning about risks of exposure or suggesting tips to reduce exposure. Other notifications may include tips, medical information, contact information, facts, instructions, helpful illustrations, error notices, countdowns, functions, and other information associate with the user's use of the computing device or health related.

The user may select or enter preferences, in some cases. The user may input preferences or update already entered user preferences. Entered or adjusted preferences may be stored in association with the user, user account, or user identification. The entered preferences may be used to determine preferences and setting adjustments in the future and may be used to control the settings and/or to update or determine the likelihood of user preferences of settings during device use.

Settings and exposure to certain light may impact the health and wellbeing of the user. It may also impact the user experience. Thus, the module(s) of the application may determine a score. The score is based on values assigned to certain device settings, user information, and other data regarding the user and the device. The application then uses the values to determine a score ("eyescore"). In some embodiments, scores may be used to determine control and adjustment of device settings. In other examples, the score may be used to manage more than one user computing device. In this way, the system may track personally recognized data across multiple devices running APs on either PCs, smartphones, tablets, or other types of equipment. This data can be shared from and to the local software with a new novel cloud service that collects information across multiple devices. Access may use cloud account data or device data. The information may run locally or optionally be further passed on to SW on a PC or other primary computing device via an I2C or USB or other available interface for purposes of partial or full implementation of the claims across the display and PC. In some instances, a separate network display may mean a monitor.

In one instance, an admin may universally or selectively remotely manage the score settings and monitor the scores. Scores may be used to allow companies to negotiate with healthcare providers or modify device settings universally or selectively. Based on the score, notifications may be sent about the exposure of employee(s) scores. The employee may receive a notification, depending on the score and certain settings or use. The scores may also determine updated settings, notifications, thresholds, adjustments, and management of the device for the user experience. The score may also suggest a different use of the device by the user. In some instances, score(s) may change settings and thresholds.

AI may be applied for analyzing and improving determination of healthy use standards and settings, making adjustments and notifications as a result of scores and score patters. Regulated use may also be adjusted, such as daily, weekly, monthly, etc. use and settings of the device. The system may execute machine learning techniques and AI techniques to implement system learning and training, so during the user experience, AI may include subroutines and the module(s) developing routines and subroutines. It may also include neural networks. The training, or learning, may improve preferences of the user's computing device environment and settings. In some instances, the user may enter preferences, or the system may include them. One non-limiting instance is with keystrokes when the user enters and makes mistakes and then corrects the mistake. The system learns the keystroke of the repeated mistake and helps the user correct the mistake. Training may also determine modifications made to the system, system settings, computing device settings, video frames, notifications, time periods, and other areas that impact the user experience. The system learns what may or may not be part of the display output based on user and system preferences. The determinations made at the different levels and acquisition of additional data through AI techniques may allow the executed application to better acquire face expressions, gestures, movement, obstructions, positions, biometrics and other possible user information. In some instances, this acquired data may become part of the score and in some instances the score is not based on this information. The data is stored as is the score in association with a user.

In some embodiments, the display colors may be adjusted of the captured data. The modules may be used for real-time image processing. In this instance, video images may be received by the module and processed. The module may detect and modify the graphical user interface display outputs. In one embodiment, color outputs may be adjusted and certain brightness values may be adjusted. One potential application for non-limiting illustration purposes only may include a video and the module may detect certain colors or patterns or images. When certain colors or patterns are detected, modules may modify the colors and brightness levels, and thus, modify the output video image. In one embodiment, the dosimeter or other processors may factor in content, such as determining the amount of blue light in red, green, and blue, tracking data by frame. A video frame or photo may include a person with blemishes, and the module may remove the blemishes.

In another instance, certain outputs may look at certain images and learn what the user may likely modify. An excel spreadsheet may likely have the brightness changed due to the colors and likely changed by the user, but a photo may not have many changes, but perhaps some target area modifications. In this way, the module may detect and modify display outputs, and may vary with different for different output displays. The user or system may optionally choose to change some colors or color temperatures of the RGB values for windows that contain "productivity" software such as Microsoft Word, Excel, and PowerPoint. This color change would be a dynamic intelligent switch to reduce harmful blue dosage. Video (including gaming) or picture images should rightly retain their RGB content as vital to the consumption of that media.

The system may be user configurable to track dosage over time in whatever manner is specified by the user, either personally, aggregate with presence, or cumulative ON for the display. This includes optional limits and warnings for day, week, month, and total life for dosage and other factors such as blinks and squints and non-averted gaze (e.g. 20 minutes of uninterrupted attention to the screen) detected. The amount of color and brightness change allowable is optionally configurable by the user. Thresholds may be used to determine warnings or adjustments. The dosage may be determined by calculating the radiance dosage as well as the irradiance dosage based on distance of user from display. Another factor is the radiance, which may not depend on the distance, but instead the radiance can be the output of the monitor and irradiance is what reaches the user; cover both because may to have distance information and the position of the person that is looking at monitor.

In some instances, at least one module may perform AI operations that identify what is part of the graphical output, such as in the previous non-limiting embodiment, a picture of kids and when the user likely would not adjust or edit the photo, then the module may make little to no change. Through the use of AI, operations may detect better color schemes for certain areas of color. The module may analyze the application output and determine modifications for the video data stream, adjusting the stream. In some embodiment, ambient light sensed by a sensor may also cause the module to adjust the brightness of the output responsive to the ambient light of the user's environment. The AI modules may learn patterns based on colors and change the output video or display frame to frame. Additionally, it may learn user habits and preferred environment of the user. The learned patterns that the user is likely to prefer based on use and user input, the this is stored in association with the user identification.

Dynamic AI control of content may be executed by the software modules. Dynamic AI may look at the display output, either with or without considering the application executed. Focusing on content output, the software module may monitor the level of blue light of red, green blue or RGB associated signals per frame. The AI module may receive data regarding the information and use it to determine the dosage calculation. In some embodiments, radiance from the monitor or brightness of the display output is analyzed to determine user preferred settings and toxic light emissions. In one instance, a white background emits a lot of different colored light, but the system may monitor how blue the pixels and the amount of harmful radiation. However, brightness or intensity may not emit harmful blue radiation, so the system would determine if, with the real-time settings and output, toxicity of blue light or use of the computing device would likely be beneficial to the user. In the example of watching movie, each frame may be analyzed because not every pixel will be blue, so toxicity levels, settings, use, brightness, user interface, user experience, user movement and positioning, as well as all the other discussed data herein, to determine if adjustments to the frame need to be made in real-time. In the example predominantly white backgrounds during the execution of certain applications, the system would monitor the color levels and brightness levels.

The system may learn that the brightness should be reduced during execution of certain outputs and modification for lower blue light in RGB may be determined and adjusted by the system. Modifications of the output display colors, such as RGB, and the output display generally, may be adjusted based on changing color of certain color pixels and/or groups of pixelations with complimentary color schemes. Such applications may include those with spread sheets, emails, documents, tables, graphs, certain windows or websites, etc.

By these embodiments, the AI functionality is similar to the way a person learns to recognize the difference between an app like Microsoft Excel and a movie or video conference being played. Similarly, the AI can learn to recognize faces and expressions and gestures just as the human brain does. Modification of a video stream in real time to take action on the AI detection is a trivial task of changing the RGB values per pixel per frame. Image type detection and AI image processing. In some embodiments, the area of the image or frame is identified to be changed. Through these various examples, the video stream is modified intelligently.

The various modules that may run on a different scalar for operations and instructions. Operations may include determining what data and location to insure into the video stream. The module component that accomplishes this may be in the video stream, or in some embodiments, it may run parallel the feed.

Other operations may include, in some embodiments, modules may receive biofeedback data and perform operations that update health and wellness score associated with the user. AI modules may further use, in some embodiments, this data to improve the user experience and adjust settings and provide notifications at the display.

The computing device or components, such as a display or monitor, may be connected or in data exchange communication with the processor, which may be at least one of an Application Processor (AP), such as Intel, or an AMD x86, an Advanced RISC Machine ("ARM") processor, and other similar processors. Processors used to implement the application may be attached to data obtaining components, such as cameras, video cameras, sensors, microphones and other components. Sensor input may be based on the type of sensor and use of sensor data may be based on the module running the operation. Sensor data that may be processed may include, but is not limited to, presence detection, IR camera, motion, temperature, pressure, light, etc. The processors must run at a sufficient speed for real-time processing and the AI processor above can analyze the video treat and other sensor data in real-time, recognizing various inputs such as faces, expressions, gestures, presence, motion, location of hand, orientation of head, blinking, sleeping, rubbing eyes, etc. To achieve such results and implement data acquisition and modification in real-time, the embodiment may include that as the modules perform the function that runs on the processor of and passes summary data to the AP.

The hardware collects the data and, in some embodiments, it is then stored in the system. Execution of the software module(s) running on the application processor may requiring interfacing hardware components, and in some embodiments, modules, for interoperability.

The main goal of this system is to encourage digital wellness and total health. First, the system can encourage healthy screen use and total wellness by, for example, intelligently tracking screen use and adjusting light levels. The application may also provide personal wellness suggestions and triggers. Additionally, it can create a Score that identifies the user's tendency to make healthy choices and it can help prompt wellness decisions. Second, the system can be created for a wide variety of devices and applications such as, but not limited to, PC, Smartphone and TV apps, OEM (original equipment manufacturers) applications, etc.

Figure 5:
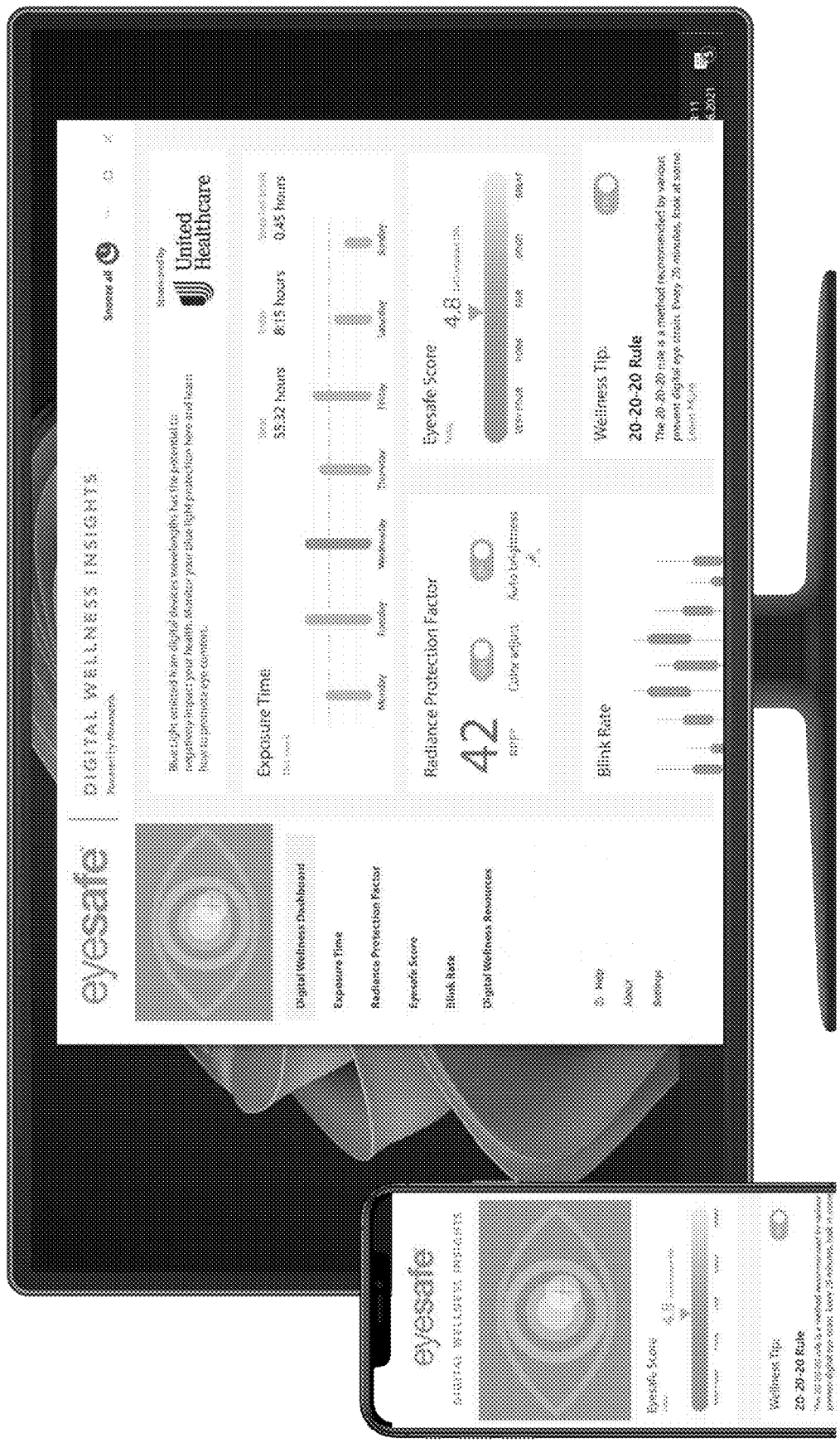
FIG. 5 illustrates digital wellness insights that may be displayed in an illustrative format.

FIG. 5 illustrates digital wellness insights that may be displayed in an illustrative format. In one embodiment, the data collected and the controls for collecting data may be displayed in a designed format, such as a dashboard. The dashboard may enable users to monitor their blue light protection and learn how to promote eye comfort. The dashboard may be referred to as a digital wellness dashboard.

In some embodiments, the software system can track parameters and exposure time. Some embodiments of the parameters tracked may include, but are not limited to, active screen time, angle of gaze, light energy output, blink rate, partial blink rate, palpebral aperture, hand to eye movement/eye rubbing, vital sensing, distance from eye to display, ambient lighting, and age/gender. By tracking these parameters, the software system can intelligently track overall screen use and adjust light levels correspondingly. The information can also provide personal wellness suggestions and triggers (for example, on the digital wellness dashboard). The blink rate may have a threshold applied, so the system can determine if the rate of blinking in a period of time is above or below the threshold, or too high or too low. If the rate is associated with a rate that would be concerning the doctor input or medical guidance may be received to communicate a notification of warning to the user, encouraging healthier habits. As the blink rate is tracked, in some embodiments, then deviations may also be tracked. deviations would be abnormalities or pattern changes. The deviations may also be sent to and determined by the system. The system may receive all the information, and more such as biometrics of obstruction/object detection and determine that user response and interaction with the device indicates a likelihood of toxic exposure or unhealthy habits, and thus, determines a notification associated with correcting the unhealthy behavior of the user or an improved setting of the computing device. Lastly, it can create a score that can identify a user's tendency to make healthy choices and can help prompt wellness decisions.

In some embodiments, hardware, such as the camera, may be used to track the above-listed parameters and may intelligently track usage and correspondingly adjust the display lighting. Exposure time may be collected and analyzed in segments, such as daily, weekly, or hourly. The totals may also be determined and displayed to allow the user to see what exposure is, and the totals may be used in the application for further determining wellness and to determine health improvement suggestions.

As a further embodiment, the application may display a score associated with the amount of exposure, level or risk, health based on digital settings and use, and other possible digital wellness insights that help determine the score. In another embodiment, the Radiance Protection Factor ("RPF") may also be identified on the dashboard and can indicate the level of protection being offered to the user in the system's current configuration (i.e., the protection offered through the combination of the physical filter and the software system).

In some embodiments, the dashboard may include controls to adjust the RPF, such as a color adjust button, toggle, switch or other user input, and possibly also an auto brightness control toggle, switch, or user input. The insights information may also provide wellness tips to the user. In some cases, the wellness tips can be shown or hidden to the user. For example, the application may provide a toggle on and off, button, or user control, that allows the user to get or hide information. In the illustration of the figure, the wellness tip includes rules or suggestions to help the user improve health or improve the user experience by reducing exposure and risk.

The application may further indicate other insights of the user data, such as the blink rate of the user. Data may be received to help track user exposure and interaction with the digital display. As illustrated, the blink rate of the user may be tracked using hardware, such as a camera, to identify the rate or number of times that a user may blink or close their eyes in a set period.

The application may also use current parameters (active screen time, angle of gaze, light energy output, blink rate, partial blink rate, palpebral aperture, and distance from eye to display, etc.), but also roadmap parameters (age/gender, partial blink rate, hand to eye movement/eye rubbing, vitals sensing, ambient lighting, etc.). There may be other key functionality used, such as intelligently tracks screen use and adjusts light levels. It may also provide personal wellness suggestions and triggers. It may, in some cases, create a score that identifies tendency to make healthy choices and helps prompt wellness decisions.

The score may indicate digital health, or health while using digital technology, and wellness index. The score may identify the likelihood to make healthy choices, prompting wellness decision and informing healthcare programs. Some inputs to determine the score may include biometrics, such as angle of gaze, blink rate, palpebral aperture, hand to eye movement/eye rubbing, temperature and vitals sensing. Inputs may also include screen usage data, such as active screen time, light energy output, distance from eye to display, and ambient lighting. Lastly, the score may further include wellness decisions made by the user such as blue light consumption, screen breaks, posture, workout detection, and standing v. sitting. The score may indicate the date or time of the allocated score. It may further indicate a message associated with the score and indicate a positive or negative message to the user. The display may also include a photo, image, or video of the user that is associated with the score.

Figure 6:
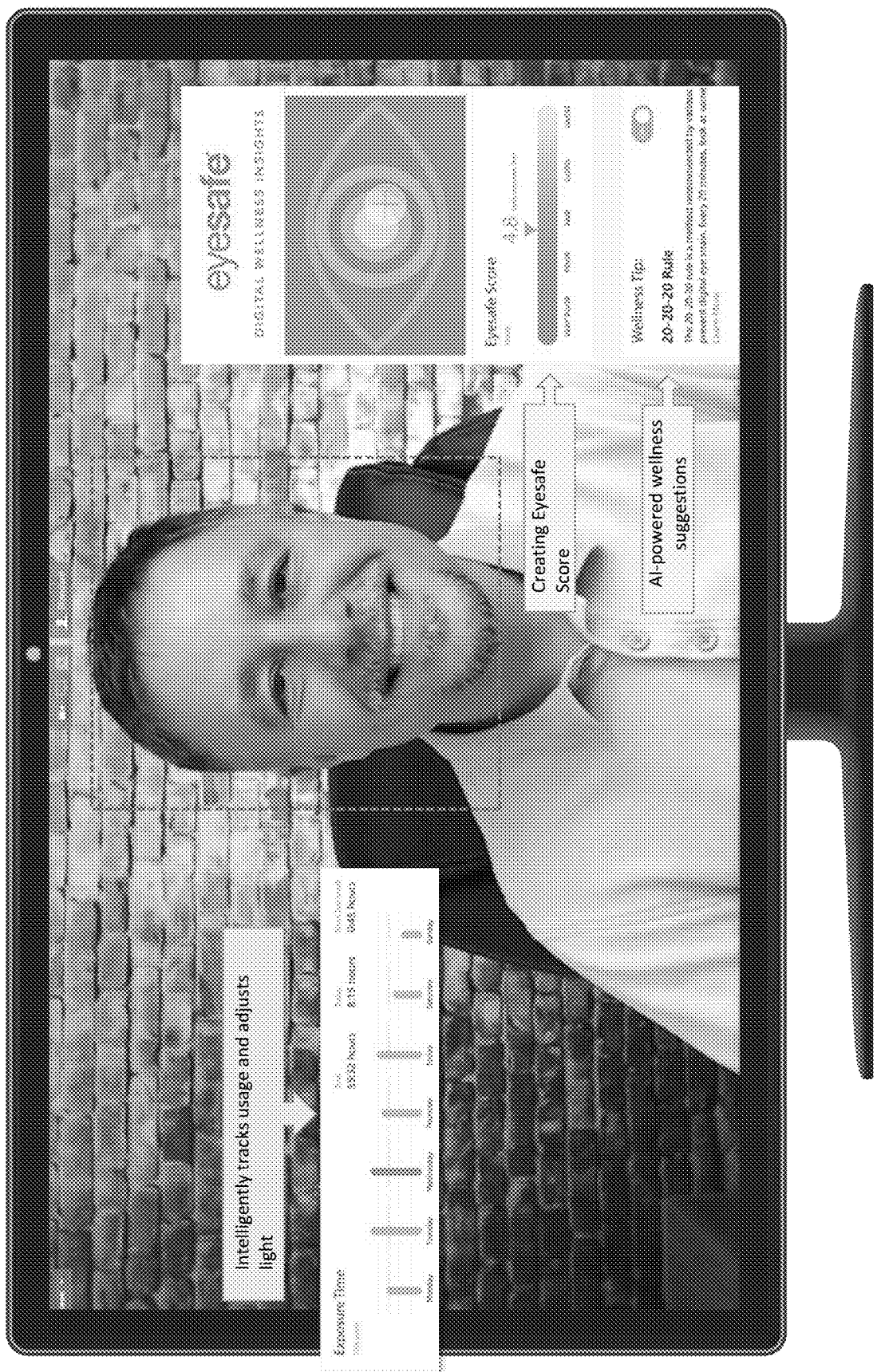
FIG. 6 illustrates and example user interface.

FIG. 6 illustrates an example user experience. As illustrated, a user may have specific data illustrated on a display. The data may be collected and analyzed as described above, and then shown to the user on the display in various formats. For example, display usage over a period of time (for example, hours, days, weeks, or months) can be shown in a graphical form so that the user can see whether their usage has been trending up or down. Further, the score associated with tracked parameters can be shown to the user, as illustrated in FIG. 6, and wellness tips can be provided to help improve the score.

The novel wellness application for digital usage as described in this application. The invention comprises at least one software program that identifies the level of high energy visible light reduction provided by the thin film; and a dosimeter for sending data about ionizing radiation to the software. The software may track the total time of device usage and determine wherein the software, based on a dosimeter measurement received from the dosimeter, communicates with at least one processor to execute at least one of determine a notification for reducing exposure to high energy visible blue light about divide user interface. The invention may further adjust the display output by at least one of adjusting a color contrast and brightness, coverage taking into account the level of visible light coverage and total time of device usage. A novel wellness application for digital usage of claim 1, wherein the software further at least one of determines blue light hazard and tracks time to determine exposure with a score that is negative, and wherein the software further blue light and tracks time to determine exposure with a score that is negative; receives facial recognition data associated with the user, and wherein the software also receives at least one of presence detection data and facial recognition associated with the user. The application may send the data from the software to a remote server in communication with other computing devices associated with the user; and receives data about the distance of the user from the computing device.

In some embodiments, the invention may further include the software uses a processor in communication with a display output, which includes at least red, green and blue light, to at least one of determine the level of blue light per frame of the display output. The application may reduce, based on the data received from the dosimeter, the display output brightness. In some embodiments, the dosimeter may receive data associated with the reduced brightness of the output display and wherein the software sends data to at least one of the output display, graphics driver, and another processor, and receives at least part of a collection of data from via EDID, or other sources. In the novel wellness application of this disclosure, the software may cause the at least one processor to change, based on the data received from the dosimeter, the display output color contrast. The at least one of the software and the dosimeter may determine a reduction value, based on data from the dosimeter, for blue light in the display output. The output display updates the output dosimeter receives data associated with the blue light of the reduction value and, in some embodiments, the software sends data to at least one of the output display, graphics driver, and another processor, and receives at least part of a collection of data from via EDID, or other sources.

In the wellness application of this disclosure, the user settings of at least one computing device and the software may be adjusted for time basis, cumulative, limits, usage monitor, time of day. The limits may be at least one of daily limits, weekly limits, and monthly limits. In some instances, color change is determined by the software when a color value is compared to a threshold and the comparison indicates the color change, and the software adjustment may be a dynamic color change that includes more change per dosage than would be given in a non-dynamic color change. The software adjustment may be a brightness change of the display output; wherein the software adjustment may be dynamic brightness change that includes more change per dosage than would be given in a non-dynamic color change; and wherein the software adjustments are made when the value of at least the brightness and color are determined to be above or below a threshold. The user settings of at least one of the computing device and the software may be adjusted based on the blink rate of an eye of the user. The blink rate is determined to be too high or too low. Tracking user information may be partially based movement and time and deviations are stored in association with the user identity; and wherein a notification is sent to the output display with a warning.

The user settings of at least one of the computing devices and the software may be adjusted based on a 20-20-20 rule associated with gaze detection. The software may determine a warning notification for display at the graphical output. The warning notification may be determined based on techniques using unfocused 3D image to change eye focus in a particular period of time; and further wherein a look away notification may be determined when monitor gaze occurs in a period of time. The computing device may be in communication with a remote network for cloud aggregation, so the software data stored locally an sent into the network that is associated with the user may be accessed by user devices in communication with the network. The data exchange in the network is traced and the data exchange includes at least one of notification warnings, functions, and countdowns.

The software may receive squinting data associated with a user, wherein AI techniques are used SW can detect this. Software data associated with the user that is received and sent into the network is aggregate data and accessible by computing devices associated with the user, and data associated with suiting that the software determines is below a threshold associated with healthy standards, then the software at least one of occurs, receives input from a healthcare provider, determine a warning associated with squinting. The application may further send a notification regarding poor focus. It may determine if the computing device settings are set at low brightness levels and determine if there are settings likely associated with causing the user to squint. The software processors may be data exchange communication with a monitor (via at least one of I2C and EDID and USB alt channel communications), real-time and per monitor detection. A novel wellness application for digital usage of claim 1, wherein the software executes dynamic AI control of content, including but not limited to the areas of: video data images frame modified. The content largely white or whitish images modified for lower blue light in red, green, and blue light (e.g. power point, excel, email). The user input to learning likelihood of preferred modifications for indicting modification should be done for display outputs and should not be done for display outputs; and changing color of certain color pixels and/or groups of pixelation with complimentary color schemes. In some embodiments, the computing device may implement executed changes is implemented in monitor scalar or in graphics driver, or in other processors. A novel wellness application for digital usage, in combination with a thin film that reduces high energy visible blue light passing therethrough.

The invention may further include a system for a novel filter and wellness application for digital usage comprising a thin film that reduces high energy visible blue light passing therethrough. The software program that identifies the level of high energy visible light reduction provided by the thin film. Additionally, the system may further include a network server that receives data from the at least one software program and is in communication with other devices that can access data sent by the at least one software program. A dosimeter for sending data about ionizing radiation to the software. The software tracks the total time of device usage and determines. The software, based on a dosimeter measurement received from the dosimeter, communicates with at least one processor to execute at least one of determine a notification for reducing exposure to high energy visible blue light about divide user interface. In some instance, the program may adjust the display output by at least one of adjusting a color contrast and brightness; coverage taking into account the level of visible light coverage and total time of device usage.

The disclosure may also include a method of using a wellness application for digital usage comprising the steps of identifying, with a software program, the level of high energy visible light reduction provided by the thin film, sending, based on a dosimeter measurement, data about ionizing radiation to the software. The software may track the total time of device usage and determines. The software, based on a dosimeter measurement received from the dosimeter, may communicate with at least one processor to execute at least one of determine a notification for reducing exposure to high energy visible blue light about divide user interface. The software may further adjust the display output by at least one of adjusting a color contrast and brightness, and coverage, taking into account the level of visible light coverage and total time of device usage.

The software may adjust the level of blue light coverage taking into account the level of visible light coverage and total time of device usage; wherein the application determines wellness indications based on received biometrics data associated with a user and the device usage. In some embodiments, the software determines a wellness score based on the level of visible light coverage and total time of device usage. The high energy visible light has at least one of a wavelength of between about 415 nm to about 455 nm, a wavelength of between about 380 nm and about 500 nm, or both.

The disclosure may further comprise biometric tracking hardware; and software that identifies the level of high energy visible light reduction provided by the thin film, wherein the hardware and software combined track data for at least active screen time, light energy output, and a biometric input, the software analyzes the tracked data to determine overall blue light exposure, the software compares the overall blue light exposure to a predetermined threshold, and the software adjusts blue light levels when the overall blue light exposure exceeds the predetermined threshold.

The system includes at least one of the biometric input is chosen from the group consisting of angle of gaze, blink rate, partial blink rate, palpebral aperture, age, gender, hand to eye movement, vitals sensing, temperature, posture, and combinations therefrom. The hardware and software may further track distance from a user's eye to the display, ambient lighting, screen breaks, physical activity levels of a user, time spent standing, time spent sitting, and combination thereof; and the overall blue light exposure is calculated as a score, and the hardware further contains a filter that reduces high energy visible blue light passing therethrough. The filter may further comprise a thin film that reduces high energy visible blue light. The software may identify the level of high energy visible light reduction provided by the thin film, wherein the software tracks the total time of device usage, and wherein the software adjusts the level of blue light coverage taking into account the level of visible light coverage and total time of device usage.

The thin film comprises an optically clear adhesive. The high energy visible blue light has a wavelength of between about 380 nm and about 500 nm. The filter may, in some embodiments, the high energy visible light has a wavelength of between about 415 nm to about 455 nm.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A novel wellness application for digital usage comprising:
    a thin film that reduces high energy visible blue light passing therethrough;
    at least one software program that identifies a level of high energy visible light reduction provided by the thin film; and
    a dosimeter for sending data about ionizing radiation to a software;
wherein the software tracks a total time of device usage; and
wherein the software, based on a dosimeter measurement received from the dosimeter, communicates with at least one processor to execute at least one of:
    determine a notification for reducing exposure to high energy visible blue light transmitted through a user interface; and
    adjust a display output by at least one of adjusting a color contrast and brightness, respective of visible light coverage and total time of device usage.

2. The novel wellness application of claim 1, wherein the software further executes at least one of:
    determines blue light hazard and tracks time to determine exposure with a score that is negative;
    receives facial recognition data associated with a user, and wherein the software also receives at least one of: presence detection data and facial recognition associated with the user;
    sends the data from the software to a remote server in communication with other computing devices associated with the user; and
    receives data about a distance of the user from the computing device.

3. The novel wellness application of claim 1, wherein the software uses a processor in communication with the display output, which includes at least red, green and blue light, to execute at least one of:
    determine the level of blue light per frame of the display output; and
    reduce, based on the data received from the dosimeter, a display output brightness;
    wherein the dosimeter receives data associated with the reduced brightness of the display output; and
    wherein the software sends data to at least one of the output display, graphics driver, and another processor, and receives at least part of a collection of data from via Extended Display Identification Data, or other sources.

4. The novel wellness application of claim 1, wherein the software causes the at least one processor to change, based on the data received from the dosimeter, the display output color contrast.

5. The novel wellness application of claim 1, wherein at least one of the software and the dosimeter determine a reduction value, based on data from the dosimeter, for blue light in the display output;
    wherein an output display updates the output dosimeter receives data associated with the blue light of the reduction value; and
    wherein the software sends data to at least one of the output display, graphics driver, and another processor, and receives at least part of a collection of data from via EDID, or other sources.

6. The novel wellness application of claim 1,
    wherein user settings of at least one of computing device and the software is adjusted for time basis, cumulative, limits, usage monitor, time of day;
    wherein the limits are at least one of daily limits, weekly limits, and monthly limits;
    wherein color change is determined by the software when a color value is compared to a threshold and the comparison indicates the color change;
        wherein the software adjustment is a dynamic color change that includes more change per dosage than the change being given in a non-dynamic color change;
        wherein the software adjustment is a brightness change of the display output;
        wherein the software adjustment is dynamic brightness change that includes more change per dosage than the change being given in a non-dynamic color change; and
        wherein the software adjustments are made when the value of at least the brightness and color are determined to be above or below a threshold.

7. The novel wellness application of claim 1,
    wherein user settings of at least one of computing device and the software is adjusted based on a blink rate of an eye of an user;
    wherein blink rate is determined to be too high or too low;
    wherein tracking user information is at least partially based on movement and time, and deviations are stored in association with an user identity; and
    wherein a notification is sent to the display output with a warning.

8. The novel wellness application of claim 1,
    wherein user settings of at least one of computing device and the software is adjusted based on a 20-20-20 rule associated with gaze detection;
    wherein the software determines a warning notification for display at a graphical output;
    wherein the warning notification is determined based on techniques using unfocused 3D image to change eye focus in a particular period of time; and
    wherein a look away notification is determined when monitor gaze occurs in a period of time.

9. The novel wellness application of claim 1,
wherein computing device is in communication with a remote network for cloud aggregation, so software data stored locally and sent into the network that is associated with an user is accessed by user devices in communication with the network; and
wherein a data exchange in the network is traced, and the data exchange includes at least one of notification warnings, functions, and countdowns.

10. The novel wellness application of claim 1,
wherein the software receives squinting data associated with an user;
wherein artificial intelligence techniques are used with the software to identify squinting by the user;
wherein software data associated with the user that is received and sent into the network is aggregate data and accessible by computing devices associated with the user; and
wherein data associated with squinting that the software determines is below a threshold associated with healthy standards, then the software at least one of occurs;
receives input from a healthcare provider,
determines a warning associated with squinting,
sends a notification regarding poor focus,
determines if computing device settings are set at low brightness levels, and
determines if there are settings likely associated with causing the user to squint.

11. The novel wellness application of claim 1, wherein the software processors have data exchange communication with a monitor (via at least one of I2C and EDID and USB alt channel communications), real-time and per monitor detection.

12. The novel wellness application of claim 1, wherein the software executes dynamic artificial intelligence control of content, including but not limited to the areas of:
video data images frame modified;
content largely white or whitish images modified for lower blue light in red, green, and blue light;
user input to learning likelihood of preferred modifications for indicting modification being done for display outputs and not being done for display outputs; and
changing color of certain color pixels and/or groups of pixelation with complimentary color schemes.

13. The novel wellness application of claim 1, wherein computing device implements executed changes in monitor scalar or in graphics driver, or in other processors.

14. The novel wellness application of claim 1, further comprising a network server that receives data from the at least one software program and is in communication with other devices that access data sent by the at least one software program.

15. The novel wellness application according to claim 1, wherein software adjusts the level of blue light coverage taking into account the level of visible light coverage and total time of device usage;
wherein the application determines wellness indications based on received biometrics data associated with an user and the device usage; and
wherein the software determines a wellness score based on the level of visible light coverage and total time of device usage.

16. The novel wellness application according to claim 3, wherein the high energy visible light has at least one of a wavelength of between about 415 nm to about 455 nm, a wavelength of between about 380 nm and about 500 nm, or both.

17. A method of using a wellness application for digital usage comprising the steps of:
identifying, with a software program, a level of high energy visible light reduction provided by a thin film, and
sending, based on a dosimeter measurement, data about ionizing radiation to a software;
wherein the software tracks the total time of device usage; and
wherein the software, based on a dosimeter measurement received from the dosimeter, communicates with at least one processor to execute at least one of:
determine a notification for reducing exposure to high energy visible blue light transmitted through a user interface;
adjust a display output by at least one of adjusting a color contrast and brightness; and
adjust the level of blue light coverage taking into account the level of visible light coverage and total time of device usage.

18. A novel filter and wellness application for digital usage, comprising:
biometric tracking hardware; and
software that identifies a level of high energy visible light reduction provided by a thin film, wherein:
the hardware and software combined track data for at least active screen time, light energy output, and a biometric input,
the software analyzes the tracked data to determine overall blue light exposure,
the software compares the overall blue light exposure to a predetermined threshold, and
the software adjusts blue light levels when the overall blue light exposure exceeds the predetermined threshold.

19. The novel filter and wellness application of claim 18, wherein the application includes at least one of:
the biometric input is chosen from the group consisting of angle of gaze, blink rate, partial blink rate, palpebral aperture, age, gender, hand to eye movement, vitals sensing, temperature, posture, and combinations therefrom;
the hardware and software further track distance from an user's eye to a display, ambient lighting, screen breaks, physical activity levels of an user, time spent standing, time spent sitting, and combination thereof; and
the overall blue light exposure is calculated as a score, and the hardware further contains a filter that reduces high energy visible blue light passing therethrough.

* * * * *